United States Patent [19]

Schenker et al.

[11] Patent Number: 5,329,030
[45] Date of Patent: Jul. 12, 1994

[54] PROCESS FOR THE PRODUCTION OF CONCENTRATED AQUEOUS DISPERSIONS OF α-SULFOFATTY ACIDE MONO- AND/OR DISALT

[75] Inventors: Gilbert Schenker, Erkrath; Thomas Engels, Frechen; Wolfgang Poly, Duesseldorf; Ansgar Behler, Bottrop, all of Fed. Rep. of Germany

[73] Assignee: Henkel Kommanditgesellschaft auf Aktien, Duesseldorf, Fed. Rep. of Germany

[21] Appl. No.: 50,302

[22] PCT Filed: Nov. 4, 1991

[86] PCT No.: PCT/EP91/02072
 § 371 Date: May 11, 1993
 § 102(e) Date: May 11, 1993

[87] PCT Pub. No.: WO92/08695
 PCT Pub. Date: May 29, 1992

[30] Foreign Application Priority Data

Nov. 12, 1990 [DE] Fed. Rep. of Germany ....... 4035935

[51] Int. Cl.$^5$ ............................................. C07B 45/00
[52] U.S. Cl. ......................................... 554/98; 554/97; 252/33
[58] Field of Search ................... 554/97; 252/554, 33; 584/98; 2/33

[56] References Cited

U.S. PATENT DOCUMENTS 1,926,442  9/1933  Günther et al. .................... 260/112
4,943,393  7/1990  Fabry et al. .......................... 252/554

FOREIGN PATENT DOCUMENTS 0112291  12/1983  European Pat. Off. .
0112292  12/1983  European Pat. Off. .
0328980   8/1989  European Pat. Off. .
2138038   3/1972  Fed. Rep. of Germany .
1215561  12/1970  United Kingdom .
1278421   6/1972  United Kingdom .

OTHER PUBLICATIONS

J. K. Weil, R. G. Bistline Jr., A. J. Stirton; J. Am. Oil Chem. Soc. 1957 (34) 100.
J. K. Weil, A. J. Stirton, E. W. Maurer, W. C. Ault, W. E. Palm; J. Am. Oil Chem. Soc. 1958 (35) 461.
A. J. Stirton, J. K. Weil; Surfactant Sci. Ser., vol. 2, Part 2: "Anionic Surfactants", p. 388, Marcel Dekker 1976.
cf. H. Stache, H. Grossmann, "Waschmittel", Springer-Verlag, Berlin 1985) (Cover Page Only) cf. Soap Cosm. Chem. Spec. 1975, p. 39.
Kirk-Othmer, "Encyclopedia of Chemical Technology", vol. 22, pp. 1-45 (1983).

*Primary Examiner*—José G. Dees
*Assistant Examiner*—Deborah D. Carr
*Attorney, Agent, or Firm*—Ernest G. Szoke; Wayne C. Jaeschke; Real J. Grandmaison

[57] ABSTRACT

The invention relates to a process for the production of concentrated mono- and/or disalt dispersions of α-sulfofatty acids by sulfonation of saturated fatty acids and/or fatty acid mixtures with sulfur trioxide, surfactants being added during the neutralization stage to improve the flowability of the dispersions.

13 Claims, No Drawings

PROCESS FOR THE PRODUCTION OF CONCENTRATED AQUEOUS DISPERSIONS OF α-SULFOFATTY ACIDE MONO- AND/OR DISALT

BACKGROUND OF THE INVENTION

1. Field of the Invention

This invention relates to a process for the production of concentrated mono- and/or disalt dispersions of α-sulfofatty acids by sulfonation of saturated fatty acids and/or fatty acid mixtures with sulfur trioxide, anionic and/or nonionic surfactants being added during the neutralization stage to improve the flowability of the dispersions. The invention also relates to the concentrated dispersions of α-sulfofatty acid mono- and/or disalts obtainable by this process.

2. Discussion of Related Art

The production of α-sulfofatty acid disalts, hereinafter referred to in short as disalts, by sulfonation of fatty acids is known per se from the literature. According to U.S. Pat. No. 1,926,442 for example, saturated carboxylic acids can be converted into α-sulfofatty acid disalts by reaction with strong sulfonating agents under drastic reaction conditions. Sulfur trioxide, oleum and chlorosulfonic acid are described as suitable sulfonating reagents. If the acidic sulfonation products accumulating during the sulfonation reaction are only partly neutralized, α-sulfofatty acid monosalts, hereinafter referred to in short as monosalts, are obtained.

In addition, it is known that disalts based on $C_{16-18}$ fatty acids are distinguished by good detergency properties, cf. in particular applicants' European patents EP 112 291 and EP 112 292.

Because monosalts can be readily converted into the corresponding disalts, for example by direct neutralization or, where they are used in detergent formulations, indirectly by the alkalinity of a detergent slurry, monosalts are also extremely important surfactants for detergents.

In practice, anionic surfactants are often used in the form of concentrated, flowable aqueous pastes in subsequent applications. Accordingly, there is a need for concentrated, flowable mono- and/or disalt pastes. Hitherto, however, concentrated and flowable mono- and disalt pastes have not been readily obtainable because the aqueous mono- and/or disalt pastes obtained in the industrial sulfonation of saturated fatty acids after partial or complete neutralization are extremely viscous above a concentration of 20 to 30% by weight and can no longer be pumped.

There is a connection between the increase in the viscosity of aqueous mono- and disalt pastes with increasing content of mono- and/or disalt in the pastes and the poor solubility of these surfactants in water. Literature data are set out in Tables 1 and 2.

TABLE 1

| Cation | Solubility of α-sulfofatty acid salts in water at 30° C. in % by weight | | | | Lit. |
|---|---|---|---|---|---|
| | $C_{16}$ Mono- | $C_{16}$ Di- | $C_{18}$ Mono- | $C_{18}$ Di- | |
| Lithium | >5 | 0.3 | >5 | | 1 |
| Sodium | 0.07 | 0.34 | 0.05 | | 1 |
| Potassium | 0.04 | 0.49 | | | 1 |
| Magnesium | 0.06 | >5 | <0.01 | | 1 |
| Calcium | 0.28 | | 0.03 | | 1 |
| Ammonium | 0.2 | 0.7 | 0.05 | | 1+2 |
| Sodium | | | | 0.1 | 2 |

TABLE 1-continued

| Cation | Solubility of α-sulfofatty acid salts in water at 30° C. in % by weight | | | | Lit. |
|---|---|---|---|---|---|
| | $C_{16}$ Mono- | $C_{16}$ Di- | $C_{18}$ Mono- | $C_{18}$ Di- | |
| ammonium | | | | | |

Lit. 1: J. K. Weil, R. G. Bistline Jr., A. J. Stirton; J. Am. Oil Chem. Soc. 1957 (34) 100

Lit. 2: J. K. Weil, A. J. Stirton, E. W. Maurer, W. C. Ault, W. E. Palm; J. Am. Oil Chem. Soc. 1958 (35) 461

TABLE 2

| Cation | Solubility of α-sulfofatty acid salts in water at 40° C. in % by weight. | | | | | Lit. |
|---|---|---|---|---|---|---|
| | Type | $C_{12}$ | $C_{14}$ | $C_{16}$ | $C_{18}$ | |
| Sodium | Mono- | 0.74 | 0.17 | 0.10 | 0.05 | 3 |
| Sodium | Di- | 7.4 | 1.5 | 0.45 | 0.14 | 3 |
| Ammonium | Mono- | | | 0.50 | | 3 |

Lit. 3: A. J. Stirton, J. K. Weil; Surfactant Sci. Ser., Volume 2, Part 2: 'Anionic Surfactants', page 388, Marcel Dekker 1976.

The problem of an industrially useful process for the production of concentrated, flowable aqueous mono- and/or disalt dispersions has not yet been satisfactorily solved by the prior art.

Accordingly, the problem addressed by the present invention was to provide an industrial process for the production of concentrated, flowable mono- and/or disalt dispersions starting out from the sulfonation of saturated fatty acids with gaseous $SO_3$.

DESCRIPTION OF THE INVENTION

The invention is based on the observation that concentrated, free-flowing pastes are obtained when anhydrous disalt powder is introduced into water. However, the production of anhydrous disalt powder requires at least one other process step, for example a physical separation process, such as crystallization, concentration by evaporation, centrifugation or filtration.

A process for the production of concentrated mono- and/or disalt dispersions of α-sulfofatty acids by sulfonation of saturated fatty acids and/or fatty acid mixtures with sulfur trioxide has now been found, in which surfactants (A) are added during neutralization with an aqueous base to form aqueous mono- and/or disalt dispersions in order to improve the flowability of the dispersions.

More particularly, aqueous mono- and/or disalt dispersions having a mono- and/or disalt content of 30 to 70% by weight and, more particularly, 40 to 60% by weight can be produced by the process according to the invention.

Surfactants (A) are understood to be substances which are either liquid in bulk or are present in the form of flowable aqueous solutions or pastes at temperatures of 60° to 90° C. and of which the molecules contain at least one hydrophobic, i.e. water-repellent, organic radical and at least one hydrophilic, i.e. water-friendly, group. The hydrophobic radicals should be saturated or unsaturated, linear or branched alkyl radicals or aryl or alkaryl radicals containing 8 to 22 carbon atoms. Suitable hydrophilic groups are sulfonate, sulfate and carboxylate groups in the form of their sodium and/or potassium salts and also ethyleneoxy and propyleneoxy groups. Examples of surfactants according to the invention are alkylbenzene sulfonate, alkane sulfonates, α-olefin sulfonates, α-sulfofatty acid methyl esters, alkylsulfates, alkylether sulfates, alcohol ethoxylates, alkylphenol ethoxylates.

Particularly suitable surfactants (A) are the sulfonation products of oleic acid and of unsaturated fatty acid triglycerides and also the adducts of 3 to 10 mol ethylene and/or propylene oxide with $C_{8-18}$ alcohols. Sulfonation products of oleic acid are known. For example, GB 1,278, 421 C describes the production of oleic acid sulfonate by reaction of technical oleic acid cuts with gaseous sulfur trioxide. Sulfonated fatty acid triglycerides have also long been known. As long ago as 1834, Runge obtained sulfonated oils by the action of sulfuric acid on olive oil and castor oil; these sulfonated oils are still used today as auxiliaries—so-called turkey red oils—in the dyeing of textiles (cf H. Stache, H. Grossmann, . "Waschmittel", Springer-Verlag, Berlin 1985). Other sulfonated oils are used in the wet crease-resistant of finishing textiles, in handwashing pastes, as thickeners in lacquers, as corrosion inhibitors or as emulsifiers for mineral oils (cf. Soap Cosm. Chem. Spec. 1975, page 39).

The fatty acids or fatty acid mixtures used as starting materials for the sulfonation reaction may be formed from vegetable or animal (land or marine animal) oils and/or fats or may be of synthetic origin, $C_{12-18}$ fatty acids largely being used. However, they may also contain relatively small amounts of fatty acids having longer or shorter chains, for example of the type present in fatty acids of vegetable and animal origin. The fatty acids or fatty acid mixtures used for sulfonation should have iodine values below 0.5 to ensure an adequate color quality of the mono-and/or disalts. Accordingly, unsaturated fatty acids have to be subjected to a hardening process (hydrogenation) before sulfonation. The hydrogenation process is carried out by methods known per se.

The sulfonation of the fatty acid may be carried out in batches or continuously. Reactors operating on the falling-film principle are particularly suitable for the process according to the invention. The key feature of this type of reactor is that, by means of suitable design measures, for example in the form of a nozzle or an overflow, the raw material to be sulfonated is fed into the reactor in such a way that it runs downwards along the tube wall in the form of a thin film while the introduction of gaseous sulfur trioxide can take place either horizontally or vertically thereto. By virtue of the rapid mass transfer and the large cooling surface, sulfonation takes place under moderate conditions in continuous falling-film reactors and generally leads to particularly light-colored products. Reactors of this type are known, for example, from DE 2 138 038; a comprehensive description can also be found in J Falbe (ed.), "Surfactants in Consumer Products", Springer Verlag, pages 61 et seq (1987) and in Kirk-Othmer, "Encyclopedia of Chemical Technology", Vol. 22, pages 1–45 (1983).

For sulfonation, the sulfur trioxide is diluted with an inert gas, preferably air or nitrogen, and is used in the form of a gas mixture containing the sulfonating agent in a concentration of 1 to 8% by volume and more particularly in a concentration of 2 to 5% by volume.

The gaseous sulfur trioxide is used in a quantity of 1.1 to 1.5 mol and preferably in a quantity of 1.2 to 1.3 mol $SO_3$ per mol fatty acid.

The fatty acids to be sulfonated are preheated to temperatures of 70° to 110° C. and more particularly to temperatures of 85° to 95° C. and are introduced into the reactor at that temperature.

After sulfonation, the liquid $\alpha$-sulfofatty acid obtained is aged for 2 to 30 minutes and preferably for 5 to 15 minutes at temperatures of 70° to 110° C. and preferably at temperatures of 80° to 95° C. In continuous operation, this process step, which is carried out to increase the degree of sulfonation, may be carried out in a heated tube (a so-called after-reaction coil) following the sulfonation reactor. Degrees of sulfonation of 80 to 95% can be established in this way.

The acidic sulfonation products accumulating during the sulfonation reaction are neutralized with aqueous bases, surfactants (A) being simultaneously added to improve the flowability of the resulting mono- and/or disalt dispersions.

Suitable neutralization bases are, in particular, ammonia, alkali metal and alkaline earth metal hydroxides. Sodium and potassium hydroxide or mixtures of these two bases are particularly suitable. The neutralization bases are used in particular in the form of aqueous solutions.

The neutralization step is generally carried out in such a way that the pH value is kept between 7 and 13 and, more particularly, between 7 and 10. Aqueous disalt dispersions are obtained in this way. However, neutralization may also be carried out in such a way that the acidic sulfonation product is only partly neutralized to the corresponding monosalts or to mono-/disalt mixtures. In this case, the neutralization step is carried out at pH values of about 3 to 7.

In one preferred embodiment of the invention, the surfactants (A) are used in a quantity of 0.1 to 30 parts by weight and, more particularly, in a quantity of 10 to 25 parts by weight active substance per 100 parts crude sulfonic acid %.

In the process according to the invention, the so-called acidic bleaching with hydrogen peroxide can be carried out before or during neutralization of the $\alpha$-sulfofatty acid to the corresponding mono- and/or disalt while the so-called alkaline bleaching with sodium hypochlorite may be carried out after the neutralization step. The acidic and alkaline bleaching and also a combination of both bleaching methods are known per se from the literature and are described, for example, in DE-PS 11 79 931, in DE-PS 12 34 709 and in DE-OS 14 43 995.

The invention is illustrated by the following Examples.

EXAMPLES

1. Analytical methods

The content of washing-active substance in aqueous surfactant pastes in % by weight (WAS content) was determined by Epton titration [DGF-Methode H III 10] while the content of unsulfonated components in % by weight (US content) was determined gravimetrically after acidification of the paste, extraction with petroleum ether and evaporation of the solvent.

2. SUBSTANCES USED

2.1 Raw materials

In the expression of the C chain distribution, the fatty acids determined are identified in an abbreviated notation. The number after the letter C signifies the number of carbon atoms in the chain. In the case of unsaturated fatty acid residues, the number of apostrophes signifies the number of olefinic double bonds present in the chain; in addition, the name of the associated fatty acid is shown in brackets.

a) Tallow fatty acid (Henkel KGaA, Düsseldorf): Iodine value: 0.5; acid value 205.0; C chain distribution: C12=0.1%, C15=0.6%, C16=27.5%, C17=2.3%, C18=65.7%, C20=1.0%, C22=0.1% (GC analysis).

b) Technical oleic acid [obtained from beef tallow] (Henkel KGaA, Düsseldorf):

Iodine value: 93.5; acid value: 201.7; C chain distribution: C12=0.1%, C14=2.7%; C14' (myristoleic acid)=0.8%; C15=0.5%, C16=4.1%; C16' (palmitoleic acid)=5.4%; C17=1.0%, C18=1.0%; C18' (oleic acid)=73.3%; C18" (linoleic acid)=8.7%; C18'''(linolenic acid)=1.0%; C20=0.1%; C20' (gadoleic acid)=1.1% (GC analysis).

c) New rapeseed oil:

Iodine value: 120; saponification value: 190; C chain distribution: C14=1%; palmitoleic acid=4%; C18=1%; C18' (oleic acid)=59%; C18" (linoleic acid)=20%; C18''' (linolenic acid)=9%; C20=1%; C20' (gadoleic acid)=2%; C22=1%; C22' (erucic acid)=1%

2.2 Anionic and nonionic surfactants a) Oleic acid sulfonate: Oleic acid sulfonate was obtained by sulfonation of technical oleic acid with SO$_3$ (cf. 2.1.b) as follows: Oleic acid was introduced at a constant rate of 550 g/hour into a continuous jacket-cooled falling-film reactor (length 110 cm, cross-section 0.6 cm) with lateral introduction of SO$_3$ (5% by volume in nitrogen). The input of the SO$_3$/nitrogen mixture was regulated in such a way that the molar ratio of olefinic double bonds present in the oleic acid (calculated from the iodine value) to sulfur trioxide was 1:0.9. The acidic reaction mixture was continuously introduced into aqueous sodium hydroxide and neutralized. The product was then heated for 120 minutes to 90° C. at a pH value of 8.5. The content of washing-active substance in the aqueous solution was measured as 50% by weight.

b) Sulfonated rapeseed oil: Sulfonated rapeseed oil was obtained by sulfonation of new rapeseed oil (cf. 2.1.c) with SO$_3$ as follows: In a continuous jacket-cooled falling-film reactor (length 120 cm, cross-section 1 cm, educt throughput 600 g/hour) with lateral introduction of SO$_3$, 5 mol rapeseed oil were reacted with 5 mol gaseous SO$_3$ (5% by volume in air) at 90° C. The acidic reaction mixture was continuously introduced into 10% by weight sodium hydroxide and neutralized. The product was then heated for 120 minutes at 95° C., the solution separating into an aqueous surfactant paste and an organic layer containing unreacted starting material. After phase separation, the organic fraction was dried in vacuo for 2 hours at 80° C. and returned to the sulfonation reaction. The aqueous surfactant solution was adjusted to a pH value of 7.8. The following data were determined:

Solids content=30% by weight (concentration by evaporation)
WAS content=0.223 milliequivalents/g
US content=4.6% by weight
SO$_4^{2-}$=3.4% by weight (ion chromatography)

c) LS4: Adduct of 4 mol ethylene oxide with a technical C$_{12/14}$ fatty alcohol (C chain distribution: C12=74%; C14=26%)

3. SULFONATION OF TALLOW FATTY ACID

In a pilot-scale falling-film reactor (manufacturer: Lurgi), a liquid tallow fatty acid (cf. 1.1.a) preheated to 90° C. was continuously contacted with air-diluted sulfur trioxide gas (5% by volume in air) at a throughput of 41.2 kg (150 mol) tallow fatty acid per hour. The molar SO$_3$ excess, based on the fatty acid, was 20%, i.e. 14.4 kg (180 mol) SO$_3$ were introduced over a period of 1 hour. The reaction was exothermic, the temperature of the crude sulfonic acid being 101° C. In a following ageing step, the crude sulfonic acid was passed through a tube heated to 90° C. (after-reaction coil). The residence time of the crude sulfonic acid in the after-reaction coil was 10 minutes. The crude sulfonic acid was then continuously further processed as described in Comparison Example 1 and Examples 1 and 2.

COMPARISON EXAMPLE 1

The crude sulfonic acid prepared as described above (cf. 3.) was continuously neutralized with aqueous sodium hydroxide at a pH value of approx. 7 and at a maximum temperature of 74° C. After the content of washing-active substance and unsulfonated components in the paste had been determined, the degree of sulfonation (S°) was calculated as follows:

$$S^\circ\ (\%) = \frac{(A)}{(A) + (B)} \times 100$$

where (A) is the fat component of the WAS content [in % by weight] which may be calculated in accordance with the following equation:

$$(A) = \frac{\text{Molecular weight fatty acid salt}}{\text{Molecular weight } \alpha\text{-sulfofatty acid disalt}} \times WAS$$

(B) is the US content [in % by weight]

The following values were obtained:

| | |
|---|---|
| WAS content: | 19.5% |
| US content: | 1.93% |
| Degree of sulfonation: | 87.5% |

An attempt to obtain disalt pastes of higher concentration by increasing the concentration of aqueous base in the neutralization step of the above process was unsuccessful. A considerable increase in viscosity meant that the disalt pastes obtained had a WAS content of at most only 27%.

EXAMPLE 1

The crude sulfonic acid prepared as described above (cf. 3.) was continuously neutralized with 13.2 kg NaOH/h in the form of a 10% by weight aqueous solution with simultaneous introduction of 17.5 kg oleic acid sulfonate/h in the form of a 50% by weight aqueous solution at a maximum temperature of 80° C. During the test, the concentration of sodium hydroxide was continuously increased while the ratio of crude sulfonic acid to oleic acid sulfonate remained constant. A pumpable paste having a WAS content of 50% by weight was obtained.

EXAMPLE 2

Pumpable disalt pastes having a WAS content of 50% by weight were obtained as described in Example 1 using sulfonated rapeseed oil and LS4 in the neutralization stage. The percentage content of these surfactants, based on the crude sulfonic acid, was 20% by weight in either case.

We claim:

1. A process for the production of concentrated mono- and disalt dispersions of α-sulfofatty acids having improved flow properties, comprising sulfonating saturated fatty acids or fatty acid mixtures, and neutralizing the sulfonated fatty acids or fatty acid mixtures with an aqueous base solution in the presence of a surfactant containing at least one hydrophobic organic radical and at least one hydrophilic group which is either liquid in bulk or in the form of a flowable aqueous solution or paste at a temperature of from 60° C. to 90° C.

2. A process as in claim 1 wherein said dispersions have a mono- and disalt content of from 30 to 70% by weight, based on the weight of said dispersions.

3. A process as in claim 1 wherein said surfactant is present in the amount of from 0.1 to 30 parts by weight, based on 100 parts by weight of unneutralized sulfonated fatty acids or fatty acid mixtures.

4. A process as in claim 1 wherein said surfactant is selected from the group consisting of alkylbenzene sulfonate, alkane sulfonate, α-olefin sulfonate, α-sulfofatty acid methyl esters, alkylsulfates, alkylether sulfates, alcohol ethoxylates, and alkylphenol ethoxylates.

5. A process as in claim 1 wherein said sulfonating step is conducted with a sulfonating agent selected from the group consisting of sulfur trioxide, oleum, and chlorosulfonic acid.

6. A process as in claim 1 wherein said surfactant is selected from the group consisting of the sulfonation product of oleic acid, the sulfonation product of unsaturated fatty acid triglycerides, and adducts of 3 to 10 moles of ethylene oxide or propylene oxide with a $C_8$–$C_{18}$ alcohol.

7. In a process for producing concentrated mono- and disalt dispersions of α-sulfofatty acids having improved flow properties by sulfonating saturated fatty acids or fatty acid mixtures, the improvement comprising neutralizing the sulfonated fatty acids or fatty acid mixtures with an aqueous base solution in the presence of a surfactant containing at least one hydrophobic organic radical and at least one hydrophilic group which is either liquid in bulk or in the form of a flowable aqueous solution or paste at a temperature of from 60° C. to 90° C.

8. A process as in claim 7 wherein said dispersions have a mono- and disalt content of from 30 to 70% by weight, based on the weight of said dispersions.

9. A process as in claim 7 wherein said surfactant is present in the amount of from 0.1 to 30 parts by weight, based on 100 parts by weight of unneutralized sulfonated fatty acids or fatty acid mixtures.

10. A process as in claim 7 wherein said surfactant is selected from the group consisting of alkylbenzene sulfonate, alkane sulfonate, α-olefin sulfonate, α-sulfofatty acid methyl esters, alkylsulfates, alkylether sulfates, alcohol ethoxylates, and alkylphenol ethoxylates.

11. A process as in claim 7 wherein said sulfonating step is conducted with a sulfonating agent selected from the group consisting of sulfur trioxide, oleum, and chlorosulfonic acid.

12. A process as in claim 7 wherein said surfactant is selected from the group consisting of the sulfonation product of oleic acid, the sulfonation product of unsaturated fatty acid triglycerides, and adducts of 3 to 10 moles of ethylene oxide or propylene oxide with a $C_8$–$C_{18}$ alcohol.

13. A process for the production of concentrated mono- and disalt dispersions of α-sulfofatty acids having improved flow properties, comprising sulfonating saturated fatty acids or fatty acid mixtures, and neutralizing the sulfonated fatty acids or fatty acid mixtures with an aqueous base solution in the presence of a surfactant containing at least one hydrophobic organic radical and at least one hydrophilic group which is ether liquid in bulk or in the form of a flowable aqueous solution or paste at a temperature of from 60° C. to 90° C., said surfactant being present in the amount of from 0.1 to 30 parts by weight, based on 100 parts by weight of unneutralized sulfonated fatty acids or fatty acid mixtures.

* * * * *